United States Patent [19]

Riedl et al.

[11] Patent Number: 4,788,358

[45] Date of Patent: Nov. 29, 1988

[54] PROCESS FOR THE MANUFACTURE OF 1,2-DICHLOROETHANE

[75] Inventors: Josef Riedl; Wenzel Kühn, both of Burgkirchen/Alz; Peter Widmann, Altötting, all of Fed. Rep. of Germany

[73] Assignee: Bayer Aktiengesellschaft, Leverkusen, Fed. Rep. of Germany

[21] Appl. No.: 762,767

[22] Filed: Aug. 5, 1985

Related U.S. Application Data

[63] Continuation of Ser. No. 362,094, Mar. 26, 1982, abandoned, which is a continuation of Ser. No. 152,996, May 27, 1980, abandoned.

[30] Foreign Application Priority Data

Jun. 1, 1979 [DE] Fed. Rep. of Germany ....... 2922375

[51] Int. Cl.$^4$ .................. C07C 17/02; C07C 17/15
[52] U.S. Cl. .................. 570/241; 570/243; 570/251
[58] Field of Search .............. 570/241, 243, 245, 251

[56] References Cited

U.S. PATENT DOCUMENTS

| | | | |
|---|---|---|---|
| 1,402,337 | 1/1922 | Backhaus | 570/251 |
| 2,716,140 | 8/1955 | McBee et al. | 570/253 |
| 3,481,995 | 12/1969 | Hartnett et al. | 570/247 |
| 3,488,398 | 1/1970 | Harpring et al. | 570/243 |
| 3,679,373 | 7/1972 | Van Camp et al. | 570/243 |
| 3,892,816 | 7/1975 | Kister | 570/245 |
| 3,992,463 | 11/1976 | Benaroya et al. | 570/245 |
| 4,206,180 | 6/1980 | Campbell et al. | 570/245 |
| 4,329,527 | 5/1982 | Kuhn et al. | 570/245 |

FOREIGN PATENT DOCUMENTS 1087703 10/1967 United Kingdom .............. 570/241

*Primary Examiner*—Howard T. Mars
*Attorney, Agent, or Firm*—Connolly and Hutz

[57] ABSTRACT

A process for the manufacture of 1,2-dichloroethane from ethylene by reaction with hydrogen chloride and inert gases containing oxygen, and also by reaction with chlorine, is described. The two chlorination reactions are carried out successively at 180° to 360° C. and under a pressure of 0.09 to 1.1 MPa in a common reaction space containing fluidized catalyst particles. A stoichiometric excess of ethylene is employed for the first chlorination reaction. The heat formed in the reaction space is removed by indirect cooling. The process is simple in terms of apparatus and permits a better re-use of the total heat of reaction of the chlorination of ethylene.

7 Claims, No Drawings

PROCESS FOR THE MANUFACTURE OF 1,2-DICHLOROETHANE

This is a continuation of application Ser. No. 362,094 filed Mar. 26, 1982 which in turn was a continuation of application Ser. No. 152,996 filed May 27, 1980 now abandoned.

The invention relates to a process for the manufacture of 1,2-dichloroethane, wherein ethylene is reacted in the gas phase in the presence of a fluidized solid catalyst, in a common reaction space, with hydrogen chloride and an oxygen-containing inert gas on the one hand and, on the other hand, with chlorine.

1,2-Dichloroethane has already been manufactured on a large industrial scale for a number of years. It is mainly converted into vinyl chloride by thermal cracking, the latter forming in turn the basis for the large-tonnage plastic polyvinyl chloride. Use for this purpose has made 1,2-dichloroethane into one of the chlorinated aliphatic hydrocarbons which are produced on the largest scale. A number of different processes are known for its manufacture, most of which start from ethylene. In general, elementary chlorine is reacted directly with ethylene in an addition reaction, this reaction being carried out at temperatures of 40° to about 120° C. in the liquid phase, frequently in 1,2-dichloroethane. In a form of this process which is much used, the considerable amount of heat formed in the addition reaction with chlorine is removed by means of boiling 1,2-dichloroethane. Since the boiling point of 1,2-dichloroethane at normal atmospheric pressure is about 84° C., the level of temperature at which the quantity of heat is removed is either insufficient to generate steam or it is only possible to obtain steam at a low temperature and thus a low level of pressure, and this steam can only be employed to a limited extent for recovering the energy contained in it.

In order to utilize in a better way the heat of reaction of the direct addition reaction of chlorine with ethylene, it is known to carry out the reaction in the gas phase in the presence of a fluidized catalyst and immediately afterwards to crack the 1,2-dichloroethane formed to give vinyl chloride. In this process the catalyst particles act as a heat transfer medium; the reaction is carried out at temperatures of 370° to 540° C. and under pressures up to 2.2 MPa, preferably 0.45 to 1.85 MPa. The hydrogen chloride formed in the cracking of 1,2-dichloroethane is used for the oxychlorination of ethylene in a separate apparatus. The 1,2-dichloroethane obtained therefrom is recycled into the fluidized bed cracking reactor.

The disadvantages of the process, such as the formation of considerable quantities of ethylene chloride, relatively large contents of unreacted 1,2-dichloroethane in the cracked products, difficulties in regulating and controlling the process and a tendency for undesirable polychlorinated hydrocarbons to be formed and for resinification and coking to take place in the cracking reactor, are stated to be reduced if fluidized, non-catalytic solids are used in the reactor instead of, for example, dehydrochlorination catalysts. Furthermore, the chlorine must be introduced in a controlled manner at a number of different points in the chlorination reaction zone in order to reduce the danger of coking. In order to do this it is necessary to put a special, relatively expensive installation into the fluidized bed cracking reactor. There is also the difficulty of separating the hot cracked gases from the fluidized, finely divided, solid heat transfer medium as completely as possible, and the disadvantage that the tubular cracking furnace for liquid or gaseous 1,2-dichloroethane, which is preferred in industry and which makes possible high throughput rates, cannot be used in this process.

A process is also known for the manufacture of 1,2-dichloroethane, in the first stage of which excess ethylene hydrogen chloride and excess oxygen in the form of air are reacted at 180° to 350° C. in the presence of a known oxychlorination catalyst, by suitably adjusting the proportions of the starting materials, with a conversion of hydrogen chloride of over 90%, and the residual gases from this stage, after extracting the unreacted hydrogen chloride by washing and after condensing, as a result of this, a major portion of the 1,2-dichloroethane formed, are reacted in a second stage at 80° to 250° C. with 80 to 120 mole % of chlorine, relative to the ethylene employed in this stage, in the presence of an iron-containing catalyst.

A similar process also operates in two separate stages, between which 1,2-dichloroethane and water are separated from the reaction product, the excess ethylene from the oxychlorination being reacted in a second stage with chlorine at a temperature of 80° to 320° C. in the presence of an activated aluminum oxide catalyst.

The reduction, by carrying out the reaction in the presence of added hydrogen chloride, of the considerable quantities of 2-chloroethanol formed in the subsequent chlorination of the excess ethylene from the oxychlorination has recently been disclosed.

Finally, a process is known in which the by-products which are formed in the chlorination of ethylene-containing gases and which are produced by chilling with water after the oxychlorination reaction and after removing the bulk of the organic products formed, are minimized by carrying out the chlorination in the presence of copper-II chloride and/or iron-III chloride on a support, as a catalyst.

All these processes mentioned above have the disadvantage that an additional reactor including a product separator and further devices is required in order to improve the yield of 1,2-dichloroethane, relative to ethylene employed, in the oxychlorination reaction. A process has now been found which enables both the oxychlorination and the direct addition reaction of chlorine with ethylene to be carried out in a common reaction space, with good yields of 1,2-dichloroethane, the temperature level of the reaction making it possible to utilize the heat of reaction, which is removed, of the addition reaction between chlorine and ethylene considerably better than in the process, which has been much used hitherto, of chlorination in boiling 1,2-dichloroethane.

The new process for the manufacture of 1,2-dichloroethane from ethylene by reaction with hydrogen chloride and inert gases containing oxygen, at 180° to 300° C. and 0.09 to 1.1 MPa, and also by reaction with chlorine in the gas phase in the presence of a solid catalyst containing a copper salt or a copper salt and an iron salt, with subsequent cooling and separation of the reaction mixture by distillation, which comprises carrying out the two chlorination reactions successively in a common reaction space, which contains fluidized catalyst particles, a stoichiometric excess of ethylene, relative to the chlorinating agent, being used for the first chlorination reaction and the heat formed in the whole reaction space being removed by indirect cooling with a liquid and/or gaseous heat transfer medium.

The two chlorination reactions can be carried out successively in any desired sequence, a high-quality grade of 1,2-dichloroethane being obtained in good yields even if the quantities of ethylene reacted in each chlorination reaction are approximately equal. The latter process is a preferred variant of the process according to the invention, if the 1,2-dichloroethane produced is subsequently converted into vinyl chloride by thermal cracking, in the customary way, since this method makes it possible for the total quantity of the 1,2-dichloroethane which is to be cracked to be produced in one reaction unit with good utilization of heat, the hydrogen chloride produced by the cracking process being recycled to the production of 1,2-dichloroethane and being used for the chlorination of about half the total quantity of ethylene employed.

Examples of suitable heat transfer media for removing, by indirect cooling, the heat formed in the whole reaction space are high-boiling mineral oils and silicon oils. It is preferable to employ water, which is converted into medium-pressure steam by absorption of heat.

In a preferred embodiment of the process according to the invention, hydrogen chloride, ethylene and an inert gas containing oxygen are first introduced into the reaction space, followed by chlorine, in the following molar ratios: 2 moles of HCl; 1.01 to 3 moles of $C_2H_4$; at least 0.5, in general 0.5 to 1, mole of $O_2$ and 0.009 to 2 moles of $Cl_2$, the quantity of chlorine being such that less than 0.001% by weight of free elementary chlorine is found in the end product of the reaction, that is to say in the mixture of gases leaving the reaction space.

An inert gas is to be understood as meaning substances which are gaseous under the reaction conditions and either do not take part in the reaction at all or only to a very minor extent. Examples of inert gases are nitrogen, carbon dioxide and 1,2-dichloroethane vapor. Nitrogen is preferably employed as the inert gas. The quantity of inert gas is appropriately such that an adequate fluidization of the solid catalyst particles is achieved, without diluting the reaction mixture too extensively.

At least 50 to 100%, especially 90 to 100%, of the total quantity of oxygen is preferably introduced into the reaction space in the form of air.

All the gases are introduced into the reaction zone at as low a relative humidity as possible. The hydrogen chloride gas preferably originates from the thermal cracking of 1,2-dichloroethane for the production of vinyl chloride. Before introduction into the reaction space, the gases can be pre-heated, for example to temperatures of 60° to 180° C.

All the gases can be introduced individually into the reaction space, but it is preferable to introduce, in each case as mixtures with one another, on the one hand hydrogen chloride and ethylene and, on the other hand, oxygen and the inert gas, for example in the form of air. The chlorine can be introduced into the reaction space at a point in time later than the introduction of the other gases in a discontinuous procedure, or, in the preferred continuous procedure, can be introduced into the reaction space at a point situated downstream of the introduction of the other gases.

The reaction space can have, for example, a spherical, ellipsoidal or cylindrical shape and it should be so designed that it has no dead corners or angles in which the fluidized catalyst can be deposited. It is preferable to use an elongated cylindrical reaction space with a circular cross-section and a vertical cylinder axis, for example a tube.

The reaction space is appropriately equipped with a double jacket and internal fitments through which the heat transfer medium flows. Examples of suitable internal fitments are serpentine coolers or tube-assembly coolers. These internal fitments can be arranged in several units separated from one another through which a variety of media can flow at various flow rates, in order to enable optimum utilization of heat and an optimum temperature pattern in the reaction space.

The various gases can be introduced into the reaction space through simple tubes, the ends of which appropriately contain devices to improve the distribution over the surface area. Examples of suitable devices of this kind are perforated plates or spheres or frits or one or more tubes having a large number of apertures for the outward flow of gas.

In its uppermost zone, the reaction space appropriately contains an aperture with a controllable cross-section through which the reaction products are removed. After leaving the reaction space, the reaction products appropriately pass through a separator for finely divided solid catalyst particles, for example a cyclone or similar apparatus. The particles separated are recycled to the reactor.

After leaving the separator, the gases are washed, if appropriate, and are partially condensed, the gas fractions which cannot be condensed at approx. 10° C. under normal pressure being passed into the atmosphere, if appropriate after removing harmful or troublesome substances. At least a part of the non-condensable gases can also be recycled to the reaction space. The condensed reaction products are separated by distillation, in the customary manner, in order to obtain pure 1,2-dichloroethane.

In a particularly preferred embodiment of the present invention the substances to be reacted are introduced into the reaction space in the following proportions: 2 moles of HCl; 1.8 to 2.2 moles of $C_2H_4$; 0.5 to 0.6 moles of $O_2$ and 0.79 to 1.2 moles of $Cl_2$. If these molar ratios are used, 1,2-dichloroethane can be produced in a single reaction unit for subsequent cracking to give vinyl chloride with optimum utilization of the hydrogen chloride recycled from the cracking process and of the starting materials ethylene and chlorine.

The process described in the preceding paragraph is carried out, in particular, in such a way that ethylene, hydrogen chloride and an inert gas containing oxygen are introduced, separately, or at least partially separated from one another, at one end of a tubular reactor, appropriately at the lower end of a vertical, or nearly vertical, tubular reactor. It is possible, for example, to introduce ethylene and hydrogen chloride together, but separately from the inert gas containing oxygen. Chlorine is introduced into the reaction space at a point separated by a specific distance in the direction of gas flow, from the last of the abovementioned gas inlets. The position of the chlorine inlet is selected in such a way that, between this inlet and the preceding gas inlet, there is a reaction space which constitutes 40 to 85%, preferably 55 to 75%, of the total reaction space available in the reactor. The reaction products are removed at the other end of the reactor, appropriately at the upper end of a vertical or nearly vertical tubular reactor.

A process of this type is suitable, in particular, for continuous operation, which is important on an industrial scale.

For this continuous operation in which, in the direction of flow of the gases, hydrogen chloride is introduced first and chlorine is introduced subsequently, the heat transfer medium in the indirect cooling system of the reaction space is preferably passed countercurrent to the gases in the reaction space. A better removal of heat and a more advantageous temperature pattern in the reaction space is achieved by this means.

In accordance with a further preferred embodiment of the process according to the invention, ethylene, chlorine and an inert gas which can optionally contain oxygen are first introduced into the reaction space, followed by hydrogen chloride and, if appropriate, oxygen and inert gas, in the following molar proportions: 2 moles of $C_2H_4$; 0.9 to 1.2 moles of $Cl_2$; 1.6 to 2.3 moles of HCl and a total of 0.35 to 1.3 moles of $O_2$, the quantity of oxygen or of hydrogen chloride being such that less than 0.001% by weight of free elementary chlorine is found in the end product, that is to say in the mixture of gases leaving the reaction space. This embodiment of the process is employed particularly if the reaction is to be carried out with a slight excess of hydrogen chloride, for example in order to minimize the content of 2-chloroethanol in the reaction products. As already described above, this embodiment is also suitable for producing 1,2-dichloroethane for thermal cracking to give vinyl chloride, with optimum utilization of the hydrogen chloride produced in this cracking reaction, the entire production of 1,2-dichloroethane taking place in a single reaction space.

Examples of suitable inert gases are again, as described above, nitrogen, carbon dioxide and/or 1,2-dichloroethane vapor, nitrogen being employed preferentially. The bulk of the oxygen required is appropriately fed in at the point at which the hydrogen chloride is also introduced, but it is also possible to feed in considerable quantities of oxygen as far upstream as the point at which ethylene and chlorine are introduced. This procedure is used particularly if it is intended to employ air as a low-cost fluidizing gas.

The process described in the two previous paragraphs is carried out, in particular, in such a way that ethylene, chlorine and an inert gas which can optionally contain oxygen are introduced, at least partially separated from one another, at one end of a tubular reactor, appropriately at the lower end of a vertical or nearly vertical tubular reactor. The inert gas can, for example, also be introduced as a mixture with chlorine, but the ethylene is introduced separately from the latter. Hydrogen chloride and, if appropriate, oxygen and inert gas are introduced into the reaction space, separately or at least partially separated, at a point separated by a specific distance, in the direction of gas flow, from the last of the abovementioned gas inlets. The position of the hydrogen chloride inlet is selected so that between this inlet and the preceding gas inlet, there is a reaction space which constitutes 10 to 40%, preferably 15 to 30%, of the total reaction space available in the reactor. The reaction products are removed at the other end of the reactor, appropriately at the upper end of a vertical or nearly vertical tubular reactor. In the embodiment of the new process which has just been described, it is advantageous to pass the heat transfer medium in the indirect cooling system of the reaction space in the same direction as the gases.

The process according to the invention is advantageously carried out at temperatures, of the reaction mixture in the reaction space, of 190° to 250° C., especially at 200° to 230° C. In this connection, particularly in the case of continuous processes, a spatial temperature gradient can be employed. For example, there can be a lower temperature at the point where the gases are introduced into the reaction space than at the point where the reaction products are removed. In the first third of the reaction space, or in the middle or in the second third of the reaction space, looking in the direction of flow of the gases, the temperature can also be higher than in the remaining zones of the reaction space.

It is appropriate to warm the gases to temperatures of 50° to about 180° C. before they are introduced into the reaction space.

The new process can be carried out under normal atmospheric pressure (0.09 to 0.1 MPa). In general, elevated pressures of up to about 1.1 MPa will be used in order to increase the space-time yield. It is preferable to carry out the reaction under pressures of 0.3 to 0.6 MPa.

The solid catalyst is advantageously employed in a finely divided form having an average particle size of 20 to 400 $\mu$m. Particularly good results are obtained using a catalyst having an average particle size of 30 to 70 $\mu$m.

The catalyst appropriately consists of a supporting substance which has a large surface per unit of weight, for example 70 to 200 $m^2/g$ or more, which is mechanically stable at high temperatures, for example up to at least 500° C., and which emerges unchanged from the gas reaction. Suitable supporting materials are heat-resistant oxides, for example silicon dioxide or aluminum oxide and also diatomaceous earth or silicate materials. Aluminum oxide is employed preferentially.

About 0.5 to 15% by weight, relative to the total catalyst, of copper in the form of a salt or oxide is appropriately applied to this supporting material. As a rule, these copper salts or oxides are converted by the hydrogen chloride present and by the chlorine, during use, into copper-II chloride, insofar as they have not already been applied initially in the form of this chloride.

Besides copper, the catalyst can advantageously also contain small quantities of Lewis acids, in particular about 0.01 to 0.5% by weight, relative to the total catalyst, of iron, applied in the form of an oxide or a salt, which is converted into the Lewis acid iron-III chloride during the reaction. The percentages mentioned above relate in each case to the metal ion, not to the chloride or other metal salt or oxide.

Besides the additives mentioned, the catalyst can also contain further additives which reduce the volatility of, in particular, the copper-II chloride, for example alkali metal chlorides, such as potassium chloride, or alkaline earth metal chlorides, such as calcium chloride or magnesium chloride, and also additives of further metallic compounds which improve the activity and/or selectivity of the catalyst in respect of the production of 1,2-dichloroethane. Examples which may be mentioned are silver, zinc, chromium, manganese, rare earth metals, such as cerium, lanthanum, ytterbium and neodymium, and platinum metals, such as rhodium and platinum.

It is also possible to use mixtures of different catalyst and catalyst support particles, for example a support material treated with copper salts and mixed with particles of the untreated support material or of another support material, for example a support material which has been treated with iron-III chloride or with another Lewis acid.

The ratio of the total reaction space before charging the catalyst to the apparent volume of the catalyst charged is appropriately about 1.1 to 3, preferably 1.2 to 1.7.

The flow velocity of the gases in the reaction space is appropriately such that at least 95% by weight, preferably 100% by weight, of the catalyst particles are fluidized. The feed rate of the inert gas which may be recycled should be selected accordingly, taking into account the gases involved in the reaction which are fed into the reaction space.

The average residence time in the reaction space of the gases present in the reaction depends on the reaction temperature chosen, it being necessary, in general, for the residence time to be shorter, the higher the reaction temperature set. In general, the average residence time is 10 to 100, preferably 20 to 70, seconds, in particular 30 to 60 seconds. In continuous operation it is determined from the volume, at the temperature and pressure prevailing in the reaction space, of the gases fed into the reaction space in one second, in relation to the volume of the whole reaction space, deducting the true volume of the catalyst contained therein and of the internal fitments (cooling tubes; temperature sensors). The true volume of the catalyst particles is determined, for example, by the liquid displacement method (see further on in the text).

In the process according to the invention it is preferable to introduce into the reaction space a quantity of oxygen, or of inert gas containing oxygen, such that 2 to 9, in particular 4 to 7, % by volume of oxygen are still present in the mixture of gases leaving the reaction space, after condensing the readily condensable reaction products (for example water and 1,2-dichloroethane) at $+10°$ C. and removing the hydrogen chloride by a customary washing process. It is advantageous, for example in regard to washing the exit gases with combustible organic solvents in order to remove residual quantities of 1,2-dichloroethane, if the $O_2$ content of the exit gas which has been pre-treated as just described, is not too high, for example less than 9% by volume. If a subsequent purification of this type is not envisaged, the oxygen content can be even higher, for example 10 to 13% by volume, very good yields of 1,2-dichloroethane still being achievable.

The separation and purification of the mixture of gases leaving the reaction space is carried out, as already described earlier in the text, by known processes.

As has also already been indicated above, the process according to the invention makes it possible, on the one hand, to convert ethylene into 1,2-dichloroethane of good quality in a single reaction unit with particularly good yields by oxychlorinating the bulk of the ethylene and post-chlorinating the remainder of the ethylene. On the other hand, the new process makes it possible, by using only one reaction unit, to make the whole quantity of 1,2-dichloroethane available in a good quality and yield for the further thermal decomposition for the production of vinyl chloride, with substantially complete re-use of the hydrogen chloride produced in the thermal decomposition. A considerable quantity of heat is formed in the reaction unit at a level of temperature which makes it possible to re-use this heat in an advantageous manner, for example as medium-pressure steam. The process does not require any apparatus or devices which are complicated, cost-intensive or susceptible to trouble; it can be carried out in equipment which is easy to clean and to maintain.

The following examples are intended to illustrate the invention in greater detail:

EXAMPLE 1

The following apparatus is used: a vertical glass tube with an internal diameter of 80 mm, narrowed at the bottom and at the top to form a gas inflow aperture and a gas outflow aperture, respectively, is used for carrying out the conversion of ethylene into 1,2-dichloroethane. This vertical reaction tube contains, immediately above the lower inflow aperture, a glass frit which extends over the whole internal cross-section of the reaction tube. A second frit is mounted a short distance above this first frit; its area amounts to about half the cross-section of the reaction tube and it is connected in its lower section to a glass tube which is carried laterally through the wall of the reaction tube. For temperature control, the reaction tube contains a coiled glass tube, the connections of which are also carried laterally through the wall of the reaction tube and which begins above the second frit and reaches a height in the reaction tube such that about 1/10 of the total length of the reaction tube, in the upper section, remains free. Between the second frit and the top of the reaction tube 6 nozzles, through which temperature sensors extend into the interior of the reaction tube, are mounted, distributed uniformly over the wall of the tube. At specific distances above frit 2, the wall of the reaction tube contains two further nozzles through which the gas inlet tubes can be led, which extend into the center of the reaction tube and are there bent vertically downwards and terminate in a perforated sphere. If the gas inlet tube is led through the nozzle which is mounted at a greater distance from the second frit, the distance between the perforated sphere and the second frit is 69% of the total internal length of the reaction space in the reaction tube. The reaction space is measured from the surface of the first frit to the point of constriction in the top section of the reaction tube. If the gas inlet tube is led through the nozzle which is nearer to the second frit, the distance from the perforated sphere of the gas inlet tube to the second frit is 17% of the total length of the reaction space in the reaction tube. The whole wall of the reaction tube is provided with a heat insulating layer.

A glass sphere is mounted above the reaction tube in order to trap catalyst particles which are entrained by the stream of gas. This glass sphere is in turn connected via a descending line to a water condenser, at the lower end of which is attached a condensate receiver with a drain cock. In its upper section, the condensate receiver contains a gas discharge tube which in turn leads into an ascending brine condenser. The constituents of the gas which are condensed here flow into a second condensate receiver with a drain cock. The non-condensable exit gases leaving the upper section of the brine condenser are passed through wash bottles in order to trap the hydrogen chloride contained therein. Samples of the washed exit gas are withdrawn for analysis by gas chromatography. The condensates which collect in the two vessels mounted below the condensers are combined and are also analyzed by gas chromatography.

The glass sphere in which the entrained catalyst particles are trapped, and also the connecting tube from the sphere to the water condenser, are provided with electrical heating sleeves. While the reactor is running, these parts of the apparatus are heated sufficiently to prevent condensate being formed in them.

The volume of the reaction space in the reaction tube, deducting the fitments contained therein (the heat control coil, the second frit, the gas inlet sphere and the temperature sensors) is 4,700 cm$^3$.

The first example is carried out by filling the reaction tube with 2.8 l (apparent volume) of a catalyst consisting of an aluminum oxide support and containing 3.7% by weight, relative to the catalyst, of copper in the form of a salt and traces of iron. The catalyst has the following sieve analysis:

| | |
|---|---|
| Particles <20μ | 25% by weight |
| Particles >20μ, but less than <70μ | 65% by weight |
| Particles >70μ | 10% by weight |

The true volume of the catalyst is determined by the water displacement method: a measuring cylinder of capacity 2 l is first filled with 1 l of catalyst particles and 1 l of water at 20° C. is added. The mixture is shaken somewhat and allowed to stand for a little time until no more gas bubbles rise to the surface. The volume of the mixture is now 1,300 cm$^3$. Accordingly, 1 l (apparent volume) of the catalyst has a true volume of catalyst particles of 300 cm$^3$. The whole catalyst charge of 2.8 l has a true volume of 840 cm$^3$. There is still a free gas space of 3.86 l in the reaction tube after the catalyst has been charged.

Air is now blown at a rate of 60 standard liters per hour through the first frit via the lower gas inlet tube and the heat control coil in the reaction tube is heated by means of a heating liquid. After about 25 minutes, an air temperature of 185° C., which does not alter further during the next 5 minutes, is determined in the reaction tube. The rate of air blown in is now increased to 90 l (S.T.P.)/hr and, at the same time, a mixture of 45 l (S.T.P.)/hr of ethylene and 44 l (S.T.P.)/hr of hydrogen chloride gas is introduced via the second frit. Immediately afterwards, the introduction of 22 l (S.T.P.)/hr of chlorine gas is also started, via the gas inlet tube which is provided with the sphere and which is mounted in the nozzle further from the second frit (the nearer nozzle is not used and is closed with a plug). All the gases fed to the reaction tube are pre-heated to 60° C.

Together with the introduction of the reaction gases, the water condenser is fed with water at +13° C. and the brine condenser is fed with cooling brine at −15° C. The exit gas wash bottles contain water as the washing liquid.

After a short time the temperature in the reaction tube has risen to 220° C. In the further course of the experiment, it is kept at this temperature by feeding the heat control coil with a cooling liquid. The exit gas leaving the brine condenser has a temperature of +10° C.

The experiment is continued for 4 hours and the exit gas composition of the washed exit gas is determined by gas chromatography after ⅓ of this period and again after ⅔ of this period. A thermal conductivity detector is used for the gases oxygen, carbon monoxide, carbon dioxide and ethylene, while a flame ionization detector is used for all the other gases indicated below. The mean values from two analyses are listed for all the examples in Table II which follows later in the text, the proportion of rare gas brought in via the air used having been already deducted from the oxygen figure.

At the end of the running time of the experiment, the gas supply to the reaction tube is terminated and the catalyst is cooled by blowing with air (at about room temperature). The condensate formed in the water condenser and the brine condenser is combined, weighed and similarly analyzed by gas chromatography by means of a flame ionization detector. The values determined for the individual Examples are listed in Table I which follows later in the text.

The following values are calculated for the experiment according to Example 1: molar ratio $HCl:C_2H_4:Cl_2:O_2=2:2.05:1:0.86$. Conversion: 96%, relative to HCl; 99.99%, relative to $Cl_2$; 97.5%, relative to $C_2H_4$. Space-time yield (relative to a reaction space of 3.86 l): 49.2 g of crude 1,2-dichloroethane$\times hr^{-1} \times l^{-1}$. Average residence time of the gases in the reaction space: 36.8 seconds.

EXAMPLE 2

The same apparatus is used as in Example 1 and the procedure followed is exactly the same as indicated in that example, with the difference that the temperature in the reaction tube is kept at 200° C. for a running time of the experiment totalling 5 hours.

The following values are determined: molar ratio $HCl:C_2H_4:Cl_2:O_2=2:2.05:1:0.86$. Conversion: 92%, relative to HCl, 99.9%, relative to $Cl_2$; 96%, relative to $C_2H_4$. Space-time yield (relative to a reaction space of 3.86 l): 48.3 g of crude 1,2-dichloroethane$\times hr^{-1} \times l^{-1}$. Average residence time of the gases in the reaction space: 38.3 seconds. For analyses see Tables I and II.

EXAMPLE 3

The procedure followed is again as in Example 1 or Example 2, with the difference that the temperature in the reaction tube is kept constant at 240° C. The running time of the experiment is 4½ hours.

The following values are determined: conversion: 98%, relative to HCl; 100%, relative to $Cl_2$; 98% relative to $C_2H_4$. Space-time yield (relative to a reaction space of 3.86 l): 49.6 g of crude 1,2-dichloroethane$\times hr^{-1} \times l^{-1}$. Average residence time of the gases in the reaction space: 35.3 seconds. For analyses of the crude 1,2-dichloroethane and of the exit gas see Tables I and II which follow.

EXAMPLE 4

The same apparatus is used as in Example 1, using the same catalyst, in terms of type and quantity.

The following quantities of gas are fed into the reaction space: air: 90 l (S.T.P.)/hr; $C_2H_4$: 27 l (S.T.P.)/hr; HCl: 44 l (S.T.P.)/hr and $Cl_2$: 4 l (S.T.P.)/hr. The temperature in the reaction tube is kept constant at 220° C.; the running time of the experiment is 3 hours.

The following values are determined: molar ratio $HCl:C_2H_4:Cl_2:O_2=2:1.23:0.18:0.86$. Conversion: 95.5%, relative to HCl; 100%, relative to $Cl_2$; 96%, relative to $C_2H_4$. Space-time yield (relative to a reaction space of 3.86 l)=28.6 g of crude 1,2-dichloroethane$\times hr^{-1} \times l^{-1}$. Average residence time of the gases in the reaction space: 44.7 seconds. For analyses of the crude 1,2-dichloroethane and the exit gas see Tables I and II which follow.

EXAMPLE 5

The same apparatus and the same catalyst in terms of type and quantity as in Example 1 are again used, but with the difference that the gas inlet tube having the spherical end is located in the nozzle on the reaction tube, nearer to the second frit, so that, as already mentioned above, the sphere of the gas inlet tube is at a distance from the second frit of 17% of the total length of the reaction space. The more distant nozzle on the reaction tube is not used; it is closed with a plug. A mixture of 90 l (S.T.P.)/hr of air and 22 l (S.T.P.)/hr of chlorine is introduced through the lower aperture of the reaction tube, entering the reaction space via the first frit. 45 l (S.T.P.)/hr of ethylene are introduced via the second frit and 44 l (S.T.P.)/hr of hydrogen chloride gas are introduced via the tube with the spherical end. The temperature in the reaction space is kept constant at 222° C.; the running time of the experiment is 3½ hours. In other respects the further procedure followed is as described in Example 1.

The following values are determined: molar ratio $C_2H_4:HCl:Cl_2:O_2=2:1.95:0.98:0.84$. Conversion: 85%, relative to HCl; 100%, relative to $Cl_2$; 92.5%, relative to $C_2H_4$. Space-time yield (relative to a reaction space of 3.86 l): 46.6 g of crude 1,2-dichloroethane$\times hr^{-1} \times l^{-1}$. Average residence time of the gases in the reaction space: 36.6 seconds. For analyses of the crude 1,2-dichloroethane and the exit gas see Tables I and II below.

In all the examples described up to now (Nos. 1 to 5), the reaction is carried out at standard atmospheric pressure of 97.3 kPa.

EXAMPLE 6

The apparatus used for this example is set up analogously to that used in Example 1, but with the difference that the reaction space used is a vertical nickel tube with an internal diameter of 50 mm which is equipped similarly to the glass tube of the apparatus used in Example 1, but with the following differences: there are only three measuring points available, distributed uniformly over the wall of the reaction tube. A frit is also inserted at the head of the tube, immediately before the constriction, this frit being used to reduce the pressure and to hold back entrained catalyst particles; the sphere provided for this purpose in the glass apparatus is omitted. A pressure-reducing valve is attached at the reactor outlet. The gas inlet tube with a spherical head is firmly built into the reactor, the distance from the sphere to the second frit (from below) being 56% of the length of the whole reaction space, measured between the bottom frit and the top frit in the tube. A pressure-measuring device is fitted in the upper part of the tube.

The volume of the reaction space, deducting the volume of the fitments located therein (temperature control coil, gas inlet tubes together with frit or spherical head and temperature sensors) is 1,500 cm$^3$. A water condenser and a brine condenser and also a hydrogen chloride washer are attached, as described in Example 1, at the reactor outlet after the pressure-reducing valve.

The nickel tube is charged with 1.2 l (apparent volume) of the same catalyst as described in Example 1. This quantity of catalyst has a true volume of 360 cm$^3$. The free space available for the gas reaction is 1,140 cm$^3$.

60 l (S.T.P.)/hr of air are first blown through the first (lowest) frit via the lowest gas inlet line and the reactor is heated to 190° C. by means of the heat control coil. The pressure in the reactor is adjusted to 392 kPa by regulating the pressure-reducing valve at the head of the reactor. A constant temperature and pressure have been reached in the reaction tube after half an hour. The quantity of air blown in is now increased to 90 l (S.T.P.)/hr and a mixture of 45 l (S.T.P.)/hr of ethylene and 44 l (S.T.P.)/hr of hydrogen chloride is blown in through the second frit. Immediately afterwards, 22 l (S.T.P.)/hr of chlorine are fed into the reactor through the gas inlet tube with a spherical head. The temperature in the reaction space increases and is adjusted to 220° C. and is kept constant for a further 6 hours, by introducing a cooling medium into the heat control coil. Gases introduced into the reaction space are pre-heated to 60° C. After the expiry of the 6 hours, the gas supply is interrupted and the catalyst in the reaction tube is cooled by blowing with air (at about room temperature).

During the whole duration of the experiment, water at +13° C. flows through the water condenser and cooling brine at −20° C. flows through the brine condenser. The exit gas leaving the brine condenser has a temperature of +11° C.

After ⅓ and ⅔ of the total duration of the experiment, samples of exit gas after the hydrogen chloride washing are subjected to analysis by gas chromatography. The mean value of the results obtained is listed in Table II which follows.

After the end of the experiment, the liquids condensed from the water condenser and the brine condenser are combined, weighed and then analyzed by gas chromatography. The analytical result is listed in Table I which follows.

The following values are determined: molar ratio $HCl:C_2H_4:Cl_2:O_2=2:2.05:1:0.86$. Conversion: 99%, relative to HCl; 100%, relative to $Cl_2$; 98.5%, relative to $C_2H_4$. Space-time yield (relative to a reaction space of 1.14 l): 169.7 g of crude 1,2-dichloroethane$\times hr^{-1} \times l^{-1}$. Average residence time in the reaction space: 43.7 seconds. For analytical results see Tables I and II.

EXAMPLE 7

The apparatus used is as described in Example 1. The reaction tube is charged with 2.8 l (apparent volume) of the catalyst described in Example 1, which has, however, been treated before use with iron-III chloride so that it contains 0.51% of iron besides 3.7% of copper. The true volume of the catalyst particles is 300 cm$^3$.

After the reaction tube has been warmed to 185° C., as described in Example 1, 90 l (S.T.P.)/hr of air are introduced through the first (lowest) frit via the lowest gas inlet tube and a gas mixture consisting of 45 l (S.T.P.)/hr of ethylene and 44 l (S.T.P.)/hr of hydrogen chloride is introduced into the reaction space via the second frit. 22 l (S.T.P.)/hr of chlorine are introduced into the reaction space via the gas inlet tube with a spherical head. The temperature in the reaction space is adjusted to 230° C. and is kept constant at this level for 5 hours by means of a cooling liquid which flows through the heat control coil. Afterwards, the gas supply is interrupted and the catalyst in the reaction space is cooled by blowing with air at room temperature.

The analyses and the evaluation of the experiment were carried out as described in Example 1. The following values were determined: molar ratio $HCl:C_2H_4:Cl_2:O_2=2:2.05:1:0.86$. Conversion: 92%, relative to HCl; 99.9%, relative to $Cl_2$; 95%, relative to $C_2H_4$. Space-time yield (relative to a reaction space of 3.86 l): 47.8 g of crude 1,2-dichloroethane$\times hr^{-1} \times l^{-1}$. Average residence time in the reaction space: 36.0 seconds. For analytical results see Table I and II, respectively.

EXAMPLE 8

The same apparatus is used as in Example 5 and the same catalyst, in terms of type and quantity, as in this example. After the reaction tube has been warmed as described in Example 1, a mixture of 72 l (S.T.P.)/hr of air and 22 l (S.T.P.)/hr of chlorine is introduced into the lowest aperture of the reaction tube through the first (lowest) frit and 37 l (S.T.P.)/hr of ethylene are introduced into the reaction tube through the second frit; immediately afterwards, 30 l (S.T.P.)/hr of hydrogen chloride are introduced into the reaction space through the gas inlet tube, the spherical head of which is at a distance from the second frit of 17% of the total length of the reaction space. The temperature in the reaction space is kept constant at 208° C. during the running time of the experiment of 2.5 hours. Afterwards, the gas supply is interrupted and cooling is carried out by blowing in air, as described several times above.

The following values are determined: molar ratio $C_2H_4:Cl_2:HCl:O_2 = 2:1.19:1.62:0.82$. Conversion: 85%, relative to HCl; 100%, relative to $Cl_2$; 95%, relative to $C_2H_4$. Space-time yield (relative to a reaction space of 3.86 l): 40.2 g of crude 1,2-dichloroethane $\times hr^{-1} \times l^{-1}$. Residence time in the reaction space: 46.1 seconds. For analyses of crude 1,2-dichloroethane and exit gas see Tables I and II which follow.

EXAMPLE 9

The procedure followed is as in Example 8, but the temperature in the reaction space is kept constant during the running time of the experiment of 3 hours at a considerably higher level, namely 246° C.

The following values are determined: molar ratio $C_2H_4:Cl_2:HCl:O_2 = 2:1.19:1.62:0.82$. Conversion: 89%, relative to HCl; 100%, relative to $Cl_2$; 96%, relative to $C_2H_4$. Space-time yield (relative to a reaction space of 3.86 l): 40.7 g of crude 1,2-dichloroethane $\times hr^{-1} \times l^{-1}$. Residence time in the reaction space: 43.6 seconds. The analyses of crude 1,2-dichloroethane and exit gas can be seen in Tables I and II, respectively, which follow.

Examples 7 to 9 are carried out at normal atmospheric pressure, that is to say at 97.3 kPa.

TABLE I

Gas chromatography analysis of crude 1,2-dichloroethane condensed

| Components | Example No. 1 % by weight | Example No. 2 % by weight | Example No. 3 % by weight | Example No. 4 % by weight | Example No. 5 % by weight | Example No. 6 % by weight | Example No. 7 % by weight | Example No. 8 % by weight | Example No. 9 % by weight |
|---|---|---|---|---|---|---|---|---|---|
| 1,2-Dichloroethane | 98.527 | 98.996 | 97.814 | 99.132 | 98.892 | 98.494 | 98.458 | 99.363 | 97.598 |
| Total of: $C_2H_2$, $C_2H_4$ and $C_2H_5$ | 0.019 | 0.003 | 0.001 | 0.010 | 0.008 | 0.001 | 0.001 | 0.013 | 0.003 |
| Vinyl chloride | 0.009 | 0.007 | 0.009 | 0.010 | 0.005 | 0.007 | 0.021 | 0.006 | 0.007 |
| $C_2H_5Cl$ | 0.030 | 0.029 |  | 0.065 | 0.066 | 0.068 | 0.034 | 0.032 | 0.037 |
| trans-1,2-Dichloroethylene | 0.009 | 0.003 | 0.015 | 0.013 | 0.004 | 0.008 | 0.028 | 0.002 | 0.014 |
| 1,1-Dichloroethane | 0.005 | 0.004 | 0.007 | 0.005 | 0.005 | 0.005 | 0.007 | 0.005 | 0.006 |
| $CCl_4$ | 0.045 | 0.033 | 0.017 | 0.011 | 0.015 | 0.021 | 0.073 | 0.017 | 0.061 |
| cis-1,2-Dichloroethylene | 0.042 | 0.021 | 0.062 | 0.058 | 0.022 | 0.038 | 0.100 | 0.012 | 0.060 |
| $CHCl_3$ | 0.024 | 0.017 | 0.009 | 0.037 | 0.007 | 0.005 | 0.044 | 0.005 | 0.033 |
| 1,1,2-Trichloroethylene | 0.002 | 0.002 | 0.003 | 0.008 | 0.001 | 0.002 | 0.006 | 0.0008 | 0.004 |
| 1,1,2-Trichloroethane | 0.882 | 0.616 | 1.054 | 0.422 | 0.662 | 0.834 | 0.807 | 0.413 | 1.361 |
| 2-Chloroethanol | 0.013 | 0.003 | 0.003 | 0.003 | 0.001 | 0.035 | 0.027 | 0.001 | 0.004 |
| 1,1,2,2-Tetrachloroethane | 0.270 | 0.163 | 0.563 | 0.084 | 0.134 | 0.250 | 0.211 | 0.041 | 0.669 |
| β,β-Dichlorodiethyl ether |  |  |  |  |  | 0.004 | 0.003 |  |  |
| Chloral | 0.112 | 0.083 | 0.178 | 0.131 | 0.175 | 0.203 | 0.130 | 0.090 | 0.127 |

TABLE II

Gas chromatography analysis of the exit gas after the hydrogen chloride washing

| Components | Example No. 1 % by volume | Example No. 2 % by volume | Example No. 3 % by volume | Example No. 4 % by volume | Example No. 5 % by volume | Example No. 6 % by volume | Example No. 7 % by volume | Example No. 8 % by volume | Example No. 9 % by volume |
|---|---|---|---|---|---|---|---|---|---|
| $O_2$ | 5.0 | 7.5 | 2.9 | 6.6 | 9.2 | 4.8 | 0.5 | 11.7 | 5.6 |
| CO | 2.0 | 1.0 | 2.5 | 1.5 | 0.90 | 1.4 | 3.4 | 0.60 | 2.4 |
| $CO_2$ | 2.1 | 1.5 | 2.8 | 2.2 | 0.86 | 2.4 | 4.4 | 0.57 | 3.0 |
| $C_2H_4$ | 0.44 | 0.98 | 0.35 | 0.60 | 3.0 | 0.25 | 0.13 | 1.9 | 0.15 |
| Vinyl chloride | 0.006 | 0.002 | 0.008 | 0.006 | 0.003 | 0.006 | 0.015 | 0.004 | 0.005 |
| $C_2H_5Cl$ | 0.016 | 0.009 | 0.179 | 0.015 | 0.034 | 0.038 | 0.016 | 0.016 | 0.020 |
| Low-boiling constituents | 0.007 | 0.004 | 0.013 | 0.006 | 0.003 | 0.021 | 0.020 | 0.001 | 0.011 |
| 1,2-Dichloroethane (EDC) | 2.4 | 2.0 | 2.15 | 2.4 | 2.4 | 2.4 | 2.2 | 2.8 | 2.8 |
| High-boiling constituents | 0.0003 | 0.0005 | — | — | <0.001 | <0.001 | 0.010 | <0.001 | <0.001 |
| 1,1,2-Trichloroethane | 0.005 | 0.002 | 0.003 | <0.001 | 0.003 | 0.003 | 0.003 | 0.001 | 0.003 |
| $Cl_2$ in the exit gas | Traces | <2 mg/hr | None | None | None | None | Traces | None | None |
| $Cl_2$ in the water | Traces | 2 ppm | None | None | None | None | 3 ppm | None | None |
| $Cl_2$ in the crude EDC | None | Traces | None | None | None | None | Traces | None | None |

We claim:

1. In a process for the manufacture of 1,2-dichloroethane by chlorination of ethylene at 180° to 300° C. and 0.09 to 1.1 MPa in the presence of a solid fluidized catalyst containing a copper salt, removing the heat formed in the reaction space by indirect cooling and recovering 1,2-dichloroethane from the reaction products after having removed said products from said reaction space, the improvement which comprises introducing separately or at least partially separated from one another hydrogen chloride, ethylene, and an inert gas containing oxygen at one end of a tubular reactor, introducing chlorine into the same reactor at a distance of 40 to 85% of the total reaction space from the last of the gas inlets for the hydrogen chloride, ethylene or oxygen-containing inert gas in the direction of flow of the gas, and the reaction products are removed at the other end of the reactor, and wherein the molar proportions are 2 moles of hydrogen chloride, 1.01 to 3 moles of ethylene, at least 0.5 mole or oxygen and 0.009 to 2 moles of chlorine with the quantity of chlorine being adjusted such that less than 0.001% by weight of free elementary chlorine is found in the mixture of gases leaving the reaction space.

2. Process according to claim 1, wherein the substances to be reacted in the reaction space are introduced in the following molar ratios: 2 moles of HCl; 1.8 to 2.2 moles of $C_2H_4$; 0.5 to 0.6 moles of $O_2$ and 0.79 to 1.2 moles of $Cl_2$.

3. Process according to claim 1, wherein the heat transfer medium in the indirect cooling system is passed countercurrent to the gases in the reaction space.

4. Process according to claim 1, wherein the oxygen is introduced in the form of air to the extent of at least 50% of its total quantity.

5. Process according to claim 1, wherein the process is carried out at temperatures, of the reaction mixture, of 190° to 250° C.

6. Process according to claim 1, wherein the process is carried out at pressures, in the reaction space, of 0.3 to 0.7 MPa.

7. Process according to claim 5 wherein the process is carried out at temperatures, of the reaction mixture, of 200° to 230° C.

* * * * *

UNITED STATES PATENT AND TRADEMARK OFFICE
CERTIFICATE OF CORRECTION

PATENT NO. : 4,788,358

DATED : November 29, 1988

INVENTOR(S) : RIEDL ET AL

It is certified that error appears in the above-identified patent and that said Letters Patent is hereby corrected as shown below:

On the face of the patent, after "Assignee:", replace "Bayer Aktiengesellschaft, Leverkusen" with --Hoechst Aktiengesellschaft, Frankfurt am Main--

Signed and Sealed this

Twenty-seventh Day of November, 1990

Attest:

HARRY F. MANBECK, JR.

Attesting Officer

Commissioner of Patents and Trademarks